United States Patent [19]

Burk et al.

[11] 4,328,171
[45] May 4, 1982

[54] PREPARATION OF CYANOACETAMIDE AND 2,2-DIBROMO-3-NITRILOPROPIONAMIDE COMPOSITIONS

[75] Inventors: George A. Burk, Bay City; Brian G. Witt; Kurt W. Swogger, both of Midland, all of Mich.; Charles A. Wilson, Pittsburg, Calif.

[73] Assignee: The Dow Chemical Company, Midland, Mich.

[21] Appl. No.: 97,468

[22] Filed: Nov. 26, 1979

[51] Int. Cl.³ .............. C07C 121/417; C07C 120/00; A01N 37/18; A01N 37/34
[52] U.S. Cl. .................................. 260/465.4; 424/304
[58] Field of Search ...................... 260/465.4; 424/304

[56] References Cited

U.S. PATENT DOCUMENTS

| | | | |
|---|---|---|---|
| Re. 29,826 | 11/1978 | Konya et al. | 424/304 X |
| 2,419,888 | 4/1947 | Nolan et al. | 424/320 |
| 3,403,174 | 9/1968 | Chance et al. | 260/465.4 |
| 3,488,734 | 1/1970 | Burk | 260/465.4 |
| 3,493,658 | 2/1970 | Schmidt et al. | 424/267 |
| 3,557,184 | 1/1971 | Toepfl et al. | 260/465.4 |
| 3,647,610 | 3/1972 | Wolf | 424/320 |
| 3,649,166 | 3/1972 | Wolf et al. | 424/304 |
| 3,668,231 | 6/1972 | Rosin et al. | 260/465.4 |
| 3,689,660 | 9/1972 | Burk et al. | 424/304 |
| 3,733,332 | 5/1973 | Toepfl et al. | 260/465.4 X |
| 3,751,444 | 8/1973 | Solem et al. | 260/465.4 |
| 3,839,583 | 10/1974 | Shema et al. | 424/304 X |
| 3,864,253 | 2/1975 | Shema et al. | 424/304 X |
| 3,865,724 | 2/1975 | Shema et al. | 424/304 X |
| 3,873,444 | 3/1975 | Shema et al. | 424/304 X |
| 3,896,231 | 7/1975 | Shema et al. | 424/304 |
| 3,897,554 | 7/1975 | Shema et al. | 424/248 |
| 3,897,562 | 7/1975 | Shema et al. | 424/304 |
| 3,915,685 | 10/1975 | Konya et al. | 424/304 X |
| 3,928,198 | 12/1975 | Brink, Jr. et al. | 424/304 X |
| 3,928,575 | 12/1975 | Moyle et al. | 424/304 X |
| 3,929,562 | 12/1975 | Shema et al. | 424/270 X |
| 3,930,015 | 12/1975 | Swered et al. | 424/304 X |
| 3,932,476 | 1/1976 | Bergeron | 260/404 |
| 4,022,605 | 5/1977 | Konya et al. | 71/105 X |
| 4,163,796 | 8/1979 | Burk | 260/465.4 X |

FOREIGN PATENT DOCUMENTS 978547 11/1975 Canada .............................. 260/465.4

OTHER PUBLICATIONS

C.A., 84:100855k, (1976).
Beilstein's Handbuch; Mainwork, vol. 2, pp. 595–596; Suppl. II, vol. 2, p. 539; Suppl. III, vol. 2, p. 1641.
Beilstein's Handbuch; MainWork, vol. 2, p. 589; Suppl. I, vol. 2, p. 256; Suppl. II vol. 2, pp. 534–535; Suppl. III, vol. 2, pp. 1632–1633; Suppl. IV, vol. 2, pp. 1891–1892.
C.A. 23:2151q, (1929).
C.A., 89:146396t, (1978).
C.A., 65:2216f, (1966).
C.A., 77:156334n, (1972).
C.A., 89:179553v, (1978).
C.A., 83:109779a, (1975).

*Primary Examiner*—Joseph Paul Brust

[57] ABSTRACT

An alkyl α-cyanoacetate is reacted with ammonia in a glycol solvent medium to form cyanoacetamide. Advantageously and without requirement of separation of the formed cyanoacetamide in glycol solvent (even though the next step and entire procedure can optionally commence with pre-formed cyanoacetamide), 2,2-dibromo-3-nitrilopropionamide is formed in situ by treating the cyanoacetamide in glycol with an appropriate mixture of bromine and an alkali metal bromate at about 10° C–40° C. Excellent and stable antimicrobial compositions may then be prepared, as part of an overall integrated process by incorporating in the resultant 2,2-dibromo-3-nitrilopropionamide-containing reaction mass an appropriate quantity of paraformaldehyde or equivalent satisfactory stabilizer at a suitably adjusted pH level.

15 Claims, 2 Drawing Figures

PREPARATION OF CYANOACETAMIDE AND 2,2-DIBROMO-3-NITRILOPROPIONAMIDE COMPOSITIONS

BACKGROUND OF THE INVENTION

Prominent amongst its applications, 2,2-dibromono-3-nitrilopropionamide (i.e., "DBNPA") finds beneficial use as a microbiocide. Satisfactory antimicrobial compositions including same are oftentimes comprised of a recipe containing:

| Ingredient | Percent by Weight in Composition | |
| --- | --- | --- |
| | Broad | Preferred |
| DBNPA | 0.1–40 | 5–20 |
| Tetraethylene Glycol (i.e., "TEG" or Equivalent) | up to 60 | 40–60 |
| Water (H$_2$O) | 20–99 | 20–60 |
| Paraformaldehyde (or other Stabilizer) | up to 2 | 0.1–1.0 |
| Sodium Bromide (NaBr) | up to 20 | 1–5 |

(pH of composition adjusted to about 3–5 with sodium carbonate, or equivalent)

DBNPA has been made pursuant to various reactions including the bromination of cyanoacetamide (i.e., "CA") in aqueous solution. DBNPA made by such procedures sometimes must be isolated as a product before being formulated into an antimicrobial composition.

The CA to be synthesized into DBNPA has been prepared by conversion of a starting alkyl α-cyanoacetate (i.e., "Alk-CA") by means of ammonolysis in an aliphatic alcohol or water medium. In such conversions, however, the CA is obtained as a solid precipitate in the reaction mass which is difficult to handle and must be separated as a solid for DBNPA manufacture or other desired purposes.

Relevant prior art involving the preparation of CA and DBNPA and formulation of the latter into antimicrobial preparations is in the Listing of References in the attached Appendix.

Nothing in prior art appears to teach a method for the manufacture of CA, DBNPA or utile antimicrobial compositions of DBNPA as advantageous as the method disclosed herein.

FIELD AND PURVIEW OF THE INVENTION

The present invention concerns procedural means and techniques, advantageously performed in integrated and unitary fashion, for the preparation and in situ formation of either CA, DBNPA or antimicrobial compositions of DBNPA in fully-formulated, stable condition in such a way that:

(a) maximized overall production economy is achieved;
(b) solids formation and handling equipment for same are avoided throughout any segment or all of the procedure;
(c) required labor for any segments of the procedure, especially the first two and including in the fully back-integrated operation, is materially reduced;
(d) bromination of CA in a glycol without substituting the hydroxyl or replacement of carbon-attached hydrogens in the glycol is accomplished;
(e) there is no problem caused by presence of a toxic waste stream when DBNPA is being made; and
(f) any or all of the possible products procurable in any step of the procedure are obtained in excellent quality and yield.

The achievement and provision of all indicated are amongst the principal aims and objectives of the invention; with other benefits and advantages becoming more evident in the ensuing description and specification.

SUMMARY OF THE INVENTION

The present invention pertains to an improved method of making CA, DBNPA or stabilized antimicrobial compositions of DBNPA by practicing any one or more of the following steps in sequence and in situ:

(1) making CA by ammoniating at a temperature in the range of 10°–80° C. under atmospheric or any other pressure (including in vacuo) a Formula (I) Alk-CA (as hereinafter defined) dispersed in a glycol solvent (as hereinafter defined) using NH$_3$ for the reaction (preferably in excess if the reaction goes to completion); then and optionally (2) directly brominating the alcohol-free CA-containing reaction mass of the first step (or, if desired, CA from any other source dispersed in glycol) with a brominating agent combination of about one mole of bromine and about ⅙ mole of an alkali metal bromate per each mole of CA in the reaction mass at a temperature in the range of about 0°–50° C. under ambient pressure and with low pH conditions; then and further optionally (3) converting the DBNPA-containing reaction mass of the second step to a stabilized antimicrobial composition by neutralizing it with an antacid and stabilizing it with paraformaldehyde or equivalent stabilizer after adjusting the glycol and water content to provide a product antimicrobial composition of the recipe within the composition set forth in the foregoing Background of the Invention section of this specification.

Suitable materials for utilization, as well as working proportional details, preparation conditions and parameters and other significant specifics of the invention are also set forth in the following specification.

ILLUSTRATED EXEMPLIFICATION OF THE INVENTION

The schematic portrayals in the two figures of the accompanying drawing are in the nature of simplified block-flow diagrams.

FIG. 1 generally illustrates the manufacture of DBNPA antimicrobial compositions according to the prior art. For purposes of comparison, FIG. 2 demonstrates the integrated and unitary, overall in situ process of the present invention.

The ammoniation and halogenation reactions involved herein are well-known in the art.

DETAILED DESCRIPTION OF THE INVENTION

Figure 1:
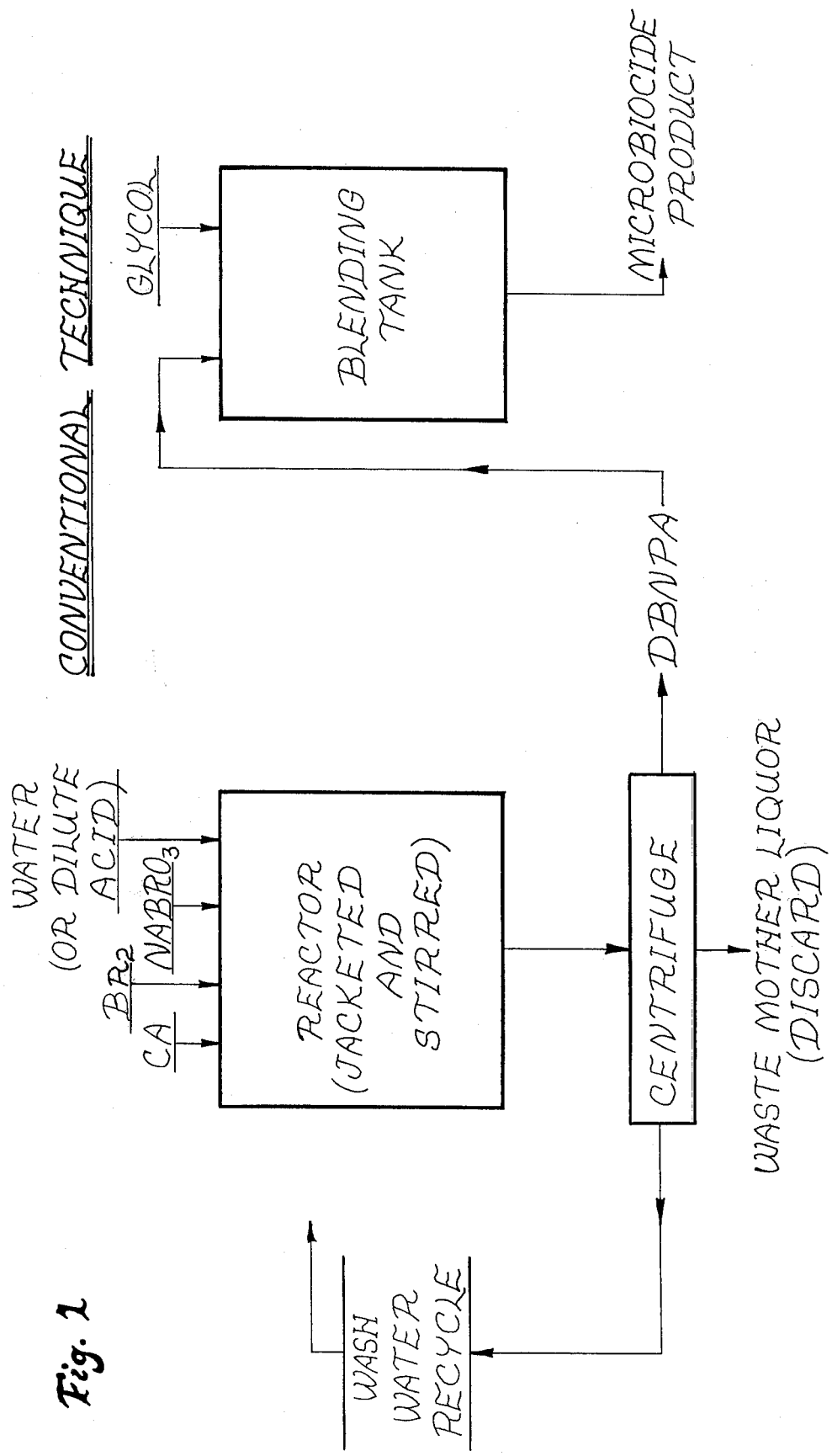
Figure 2:
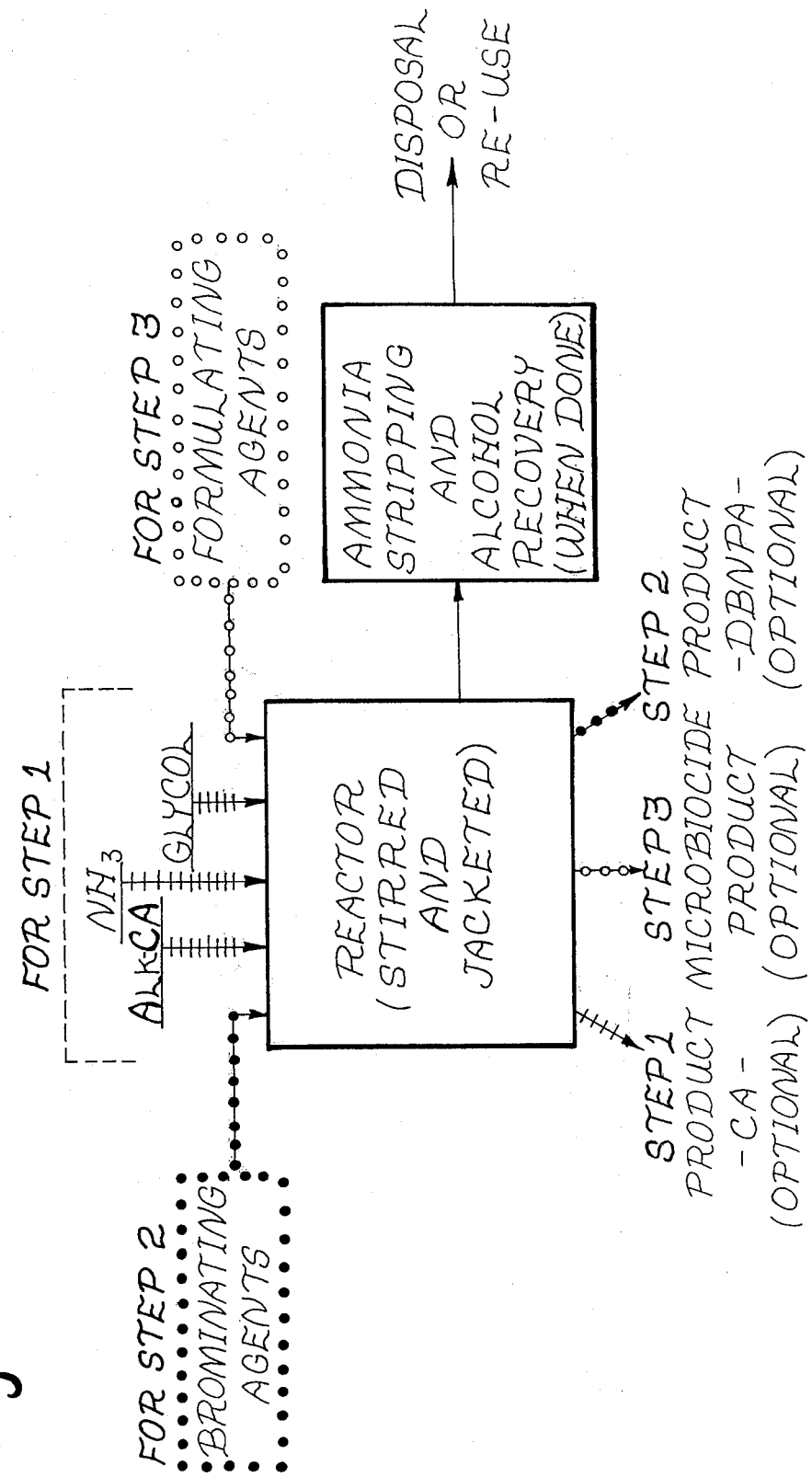

The present invention may be accomplished by practicing either at least the first and/or then, if desired, the second or both of the following steps in sequence or using CA from any source dissolved in glycol again followed, if desired, by the third step. All of this is explained and defined in association with the following formulae and equations for the first two steps and detailing of the third.

First Step

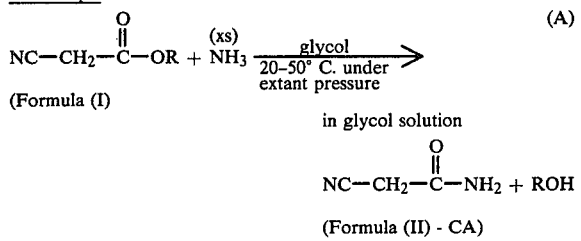

(Formula (II) - CA)

wherein R is either: an alkyl unit containing from 1 to about 20 carbon atoms, advantageously a lower alkyl of 6 carbon atoms or less, especially methyl (i.e., "Me"), ethyl (i.e., "Et") or isopropyl (i.e., "iPr"); or an aryl, including substituted aryl, unit containing from 6 to about 12 carbon atoms. When R is alkyl, the Formula (I) starting material is herein identified as an "Alk-CA"; and "LAlk-CA" when it is a lower alkyl.

The excess of ammonia to employ (when, as is generally the case, one is utilized) may be as great as 150 mole percent and, in some situations even greater; although it is usually adequate for only a 10–60 mole percent excess to be utilized. The important thing is to ensure having at least a molar equivalent of $NH_3$ available in the reaction mass for conversion of the sub-CA to CA. Thus, if the reaction is conducted under reduced pressure (i.e., vacuum) conditions, the excess of $NH_3$ utilized may be as much as 1,000 percent or more due in such circumstances to its rapid stripping removal from the reaction mass. In this connection, vacuum operations for performance of step one can be advantageous when LAlk-CA starting materials are being converted despite the necessity to administer much more $NH_3$ than actually needed for the reaction. This is because the lower alkyl alcohol by-product formed tends to be taken from the reaction mass more or less simultaneously with its formation.

A temperature range between about 10° C. and about 80° C. is more broadly operable, although a useful 20°–50° C. operating temperature is indicated in Equation (A) above. As indicated, the reaction may be conducted under literally any extant pressure, even though atmospheric pressure or those of up to 25 psig are usually more practical with it often occurring that the reaction is conducted under a pressure that is typically between about 5 and about 10 psig.

While excepting to allow enough for reaction completion there is nothing critical about the time limits required for same, the reaction is usually accomplished within a period of time between about ½ and 12 hours, frequently from 1 to 6 hours, depending to a large extent on precise conditions and reactants involved.

While unnecessary, some water may also be present in the reaction mass (i.e., "Rxn Mass") resulting as the end product of Equation (A). Generally, this should be in an amount, if any, not in excess of about 25 weight percent of the glycol solvent utilized. The water may come from the glycol formulation employed. Or, it may be purposely added (although this is usually extraordinary to do).

The glycol itself can be any normally (i.e., at room temperature) liquid glycol product that is non-reactive in the system and which is an effective solvent medium for the involved reactants.

These, advantageously, may be one of the common and well-known polyalkylene glycols or ethers thereof, especially a straight-chain polyalkylene glycol or a mono- or di-lower saturated hydrocarbyl ether thereof. In this, the term "saturated hydrocarbyl" refers to a monovalent saturated hydrocarbon radical as hereinbefore defined.

Generally, such polyalkylene glycols and polyalkylene glycol ethers have a weight average molecular weight (MW) of from about 75 to about 1,000. Such average molecular weights are commonly designated for a particular glycol involved by placing a numeral representing the weight average molecular weight after the glycol name.

Of particular interest for present purposes are the polyalkylene glycols of the ethylene, trimethylene or tetramethylene series; and the mono- and di-lower (e.g., containing from 1 to about 6 carbon atoms) saturated hydrocarbyl ethers thereof. Particularly advantageous solvents thus include polyethylene glycols, trimethylene glycols, tetramethylene glycols, and the mono- and di-lower saturated hydrocarbyl (e.g., lower alkyl and phenyl) ethers of such glycols. More specific examples of such glycols and ethers include 1,4-butanediol, triethylene glycol, polyethylene glycol 200, tetraethylene glycol, polyethylene glycol 400, diethylene glycol dimethyl ether, diethylene glycol phenyl ether, diethylene glycol ethyl phenyl ether, polytrimethylene glycol 200, diethylene glycol, triethylene glycol methyl ether, and polyethylene glycol 600.

Preferably, the polyalkylene glycol or ether ingredient is a polyethylene glycol, or a mixture of polyethylene glycols, having MW of from about 175 to about 250.

For most practical purposes, a polyethylene glycol having a weight average molecular weight on the order of 200 or so is utilized (the same being typified by the material obtainable from The Dow Chemical Company under the trade-designation "Polyglycol E-200"). Alternatively, such glycol ethers as the commercially-available "Dowanol" brand glycol ethers may be employed.

The concentration of the dispersed CA of the Formula (I) in the glycol solvent is usually advantageous when it is between about 5 and about 50 weight percent, based on total weight of dispersion; this preferably being between about 20 and about 30 weight percent.

If CA, per se, is desired when step one is completed, it may be removed in any satisfactory manner. If the CA is to be employed as an intermediate for DBNPA to be prepared in the following step two, it is preferred to strip or otherwise suitably remove the alcohol by-product from the Rxn Mass. Advantageously, especially with lower alkyl alcohols, this can be done by simple heating at an elevated temperature and/or reduced pressure to remove the particular alcohol. When alcohols other than those from LAlk-CA's are involved (as from long-chain alkyl or aryl units), it may be unnecessary to remove them from the Rxn Mass for its further use. The presence of such higher molecular weight alcohols is often tolerable in the step one Rxn Mass for many purposes, including bromination thereof in the DBNPA preparation.

Second Step

The Rxn Mass product of step one, freed of substantially all of the by-product alcohol is employed directly as the intermediate starting material for DBNPA preparation as illustrated in and by the following Equation (B):

Alcohol stripped Rxn Mass product of Equation (A) or CA in glycol $$\text{Br}_2 + \text{aq. NaBrO}_3 \xrightarrow[\text{atmospheric press. in glycol solution}]{10-40^\circ \text{C. at}} \text{NC}-\text{CBr}_2-\overset{\overset{\text{O}}{\|}}{\text{C}}-\text{NH}_2 \quad \text{(B)}$$

(DBNPA)

The basic, acid-catalyzed bromination procedure involved in the performance of Equation (B) involves:

$$\text{CA} + 2\,\text{Br}_2 \rightarrow \text{DBNPA} + 2\,\text{HBr}, \quad \text{(C)}$$

wherein $$6\,\text{HBr} + \text{NaBrO}_3 \rightarrow 3\,\text{Br}_2 + 3\,\text{H}_2\text{O} + \text{NaBr}, \quad \text{(D)}$$

so that the overall is, in fact:

$$3\,\text{Ca} + 3\,\text{Br}_2 + \text{NaBrO}_3 \rightarrow 3\,\text{DBNPA} + 3\,\text{H}_2\text{O} + \text{NaBr}. \quad \text{(E)}$$

The elemental bromine and sodium bromate (or equivalent bromate of an alkali metal such as potassium) are employed in molar ratios to the CA in the Rxn Mass product of Equation (A) of 1 mole of $\text{Br}_2$ and $\frac{1}{3}$ mole of $\text{NaBrO}_3$ to each mole of CA to be converted. The 3:1 molar ratio of $\text{Br}_2$ to $\text{NaBrO}_3$ should be fairly accurately observed and implemented (with a tolerance, say, of no more than ±5 mole percent).

The $\text{Br}_2$ is generally employed in elemental form, although it may be diluted if so preferred. While it may be charged as a solid, the alkali metal bromate is more often employed in an aqueous solution of a concentration between about 10 and 50 weight percent of dissolved salt, usually on the order of from about 20 to about 35 weight percent.

It is preferable to conduct the bromination reaction of Equation (B) at a pH between about 1 and 2. This facilitates having the reaction proceed quite rapidly. However, the reaction will proceed satisfactorily when the pH is kept below about 3. Above pH 3, the reaction is fairly slow and in the pH range from 4 to 6 it is almost undesirably slow. When the pH of the reaction mass is greater than about 3.5, there may be a tendency for decomposition to occur. This, of course, is best avoided.

With reference to Equation (C), the generation of HBr usually brings the pH of the reaction mass quite rapidly down from a pH of about 7 to a value of about 2. However, it must also be taken into account per Equation (D) that $\text{NaBrO}_3$ functions as both an antacid and an oxidant. In the alternative, the pH can be controlled by the addition of an alkaline material such as sodium hydroxide to convert the HBr to NaBr. Thus, there can be times when the pH of the reaction mass may tend to rise to an unwanted high value.

This can be corrected by adding supplemental acid, preferably HBr, in small amounts during the course of or especially in the latter stages of the reaction of Equation (B) to maintain the pH of the reaction mass below about 3.5. Other acids can be used for the same purpose including, for example, hydrochloric, phosphoric, sulfuric, and so forth.

The reaction of Equation (B) is relatively exothermic in nature. Means to control the temperature of the reaction mass must be provided. For this reason, it is often beneficial to add the $\text{Br}_2$ and $\text{NaBrO}_3$ in alternatively-charged portions during the entire reaction. Each incremental charge of the $\text{Br}_2$ and $\text{NaBrO}_3$ reagents may comprise about 2–3 percent, often 2.5 percent, of the total input. Variations in the size of the aliquot portions may be made. In fact, the $\text{Br}_2$ and $\text{NaBrO}_3$ may be added during the course of the reaction in simultaneously-fed continuous streams. If the heat transfer capability of the equipment is adequate for efficient control of reaction temperature, all or considerable portions of the required $\text{Br}_2$ and $\text{NaBrO}_3$ may be added at the start of the reaction. The essential condition to observe is the acidity of the reaction mass.

The bromination of Equation (B) is usually accomplished within a time period of from about $\frac{1}{2}$ to about 24 hours, depending on size of equipment utilized and volume of reaction mass being handled, especially in batch processing. In smaller apparatus and with lower volume reaction masses (as in laboratory- and/or pilot plant-sized units), the bromination may be done within a 12-hour period and sometimes even as quickly as within about 4 hours. It is frequently beneficial after completion of the reaction of Equation (B) to continue the reaction conditions for a post reaction period between about 5 minutes and about 4 hours. This tends to ensure thorough finishing of the involved reaction.

A broader range of permissible operating temperature than the 10°–40° C. span indicated in connection with Equation (B) is one of from about 0° C. to about 50° C. There is generally no need to nor advantage in running the second step under pressure; atmospheric conditions being ordinarily quite satisfactory for this.

If DBNPA, per se, is desired, it may be isolated by any suitable technique from the Rxn Mass product of Equation (B). The Rxn Mass product of Equation (B) can be employed for antimicrobial compositions from the second step product according to the following third step.

Third Step

The Rxn Mass product of Equation (B), as indicated, can be readily converted by final formulation, blending and stabilization without necessity for any refinement thereof. Thus, an excellent antimicrobial composition of established utility pursuant to the recipe set forth in the foregoing Background of the Invention section of this specification can be prepared by adjusting the water and glycol contents to any desired respective levels then neutralizing the composition with $\text{Na}_2\text{CO}_3$ (or equivalent antacid) to the prescribed 3–4 pH range (with pH 3.5 frequently being a desirable level); and incorporating an appropriate stabilizing amount of, preferably, paraformaldehyde (i.e., "p-FORM") in the composition being made. If desired and as in hereinafter more fully disclosed, other stabilizers equivalent to it for present purposes can be employed in place of (or sometimes in combination with) p-FORM. If desired, the sequence of neutralization and stabilizer additions can be reversed or done simultaneously. The formulation is ordinarily done in simple fashion with conventional liquid blending equipment following which the antimicrobial product composition is suitably packaged.

As mentioned, p-FORM is a preferred stabilizer for the step three formulations prepared in practice of the present invention. Other stabilizers which may be used are disclosed in several commonly owned Applications for U.S. Letters Patent which were all filed Dec. 14, 1977. Examples of such optional stabilizing ingredients thus include: acids or anhydrides (e.g., acetic acid, ethylenediaminetetraacetic acid, succinic acid, succinic anhydride, glycolic acid, etc.) as disclosed by George A. Burk in application Ser. No. 860,498, filed Dec. 14, 1977, now abandoned, and in application Ser. No.

043,064, filed May 29, 1979, now U.S. Pat. No. 4,241,080; carbamoyl or sulfamoyl compounds (e.g., N-methyl urea, N,N-diethyl urea, biuret, sulfamide, oxamide, N,N-dimethylformamide, caprolactam, N-methyl-2-pyrrolidone, dimethylhydantoin, succinimide, etc.) as disclosed by George A. Burk and Charles E. Reineke in U.S. Pat. No. 4,163,797; cyclic ethers (e.g., 1,4-dioxane, tetrahydrofuran, sym-trioxane, N-methyl morpholine, etc.) as disclosed by George A. Burk and Charles A. Wilson in application Ser. No. 860,497, filed Dec. 14, 1977, now U.S. Pat. No. 4,190,668; aldehydes additional to p-FORM (e.g., formaldehyde, vanillin, etc.) as disclosed by George A. Burk, Charles A. Wilson and Charles E. Reineke in U.S. Pat. No. 4,163,798; quaternary ammonium or phosphonium salts (e.g., methyl triphenyl phosphonium bromide, n-$C_{12}$-$C_{18}$ alkyl dimethyl benzyl ammonium chloride, etc.) as disclosed by George A. Burk in U.S. Pat. No. 4,163,796; and azine or nitrile compounds (e.g., cyanuric acid, 2-chloro-4,6-bis(ethylamino)-s-triazine, cyanoguanidine, succinonitrile, etc.) as disclosed by George A. Burk in U.S. Pat. No. 4,163,795.

The pH adjustment of the final microbiocide formulations enhances their stability, especially over prolonged periods of storage. While $Na_2CO_3$ is a convenient, inexpensive and effective antacid to employ for pH adjustment of the formulation from the acidic Rxn Mass of step two, other neutralizing agents are also capable of being used for the purpose. These, merely by way of illustration, include such materials as other alkali metal carbonates, alkali metal bicarbonates, and organic bases such as hexamethylenetetramine and pyridine, as well as the so-called Schiff's Base materials. While it is much preferred to employ weak bases for pH adjustment of the formulations, it is possible if appropriate care is taken with their inclusion to utilize much more alkaline substances for this. Caustic soda may be used if accompanied by rapid mixing.

As has been indicated, any and/or all of the three steps above-outlined in accordance with the present invention can be done either by batch-wise procedures or by continuous processing techniques.

It is apparent, especially when at least the first two and particularly when all three sequential and unitary steps are followed to prepare either DBNPA or a product antimicrobial composition, that the overall preparation eliminates the need for separation and handling of CA and/or DBNPA. When all three steps are utilized for microbiocide product preparation the relatively small quantities of impurities in the final formulation are of the types that result from use of the antimicrobial material. Thus, there is no difficulty in the utilization of such antimicrobial compositions.

The antimicrobial products obtained by operation of all three sequential steps in practice of the invention are noteworthy in their exceptionally good stability during storage.

Working Exemplifications of the Invention

The following illustrative examples show the simplicity in and great benefit from reduction to practice of the present invention. Unless otherwise specified in given instances: all "parts", "proportions" and "ratios" are to be taken by weight; and "percentages" given are by weight, based on total weight of involved composition or reaction mass. All temperature readings are in °C.

First Illustration (Involving gaseous $NH_3$ addition to EtCA in TEG)

A 3-neck reaction flask was equipped with a motor stirrer, cooling bath, thermometer, $NH_3$-inlet tube, and a reflux condenser vented to a water scrubber containing 20 ml of concentrated aqueous hydrochloric acid.

There was first charged to the flask 200 g of TEG and 115 g of EtCA, with commencement of slow stirring. Into the gently mixing liquid there was then introduced 40 g of gaseous $NH_3$ (115 percent of molar requirements) at 15°-32° C. over a one-hour period. The reactor was also equipped with a trap to collect the ethanol by-product of the reaction. The temperature was then raised to 175° C. during a one-hour period to remove the ethanol at atmospheric pressure. A stream of $N_2$ gas was then purged through the liquid reaction mass for a short period to remove the last traces of ethanol from the system. The ethanol collected was 88 percent of theory.

The reaction mass, cooled to 24° C., resembled a thick slush which, when heated to 30° C., became easily stirrable.

Bromination was then carried out in the reaction mass by alternate incremental additions of bromine and a solution of sodium bromate. For this, one mole (160 g) of $Br_2$ and $\frac{1}{3}$ mole of $NaBrO_3$ (50 g in 160 ml of tap water) were added over a period of one hour. The reaction temperature was maintained at 30°-36° C. by an ice bath. After a two-hour reaction period, the resulting solution assayed 34.5 percent DBNPA.

The completed DBNPA solution was diluted with more TEG and neutralized to pH 3.5 with $Na_2CO_3$. There was obtained 1100 g of a deep orange-colored liquid which assayed 20.7 percent DBNPA, indicating a 94 percent yield from the starting EtCA.

The neutralized solution was permitted to stand for about 65 hours. It was then stabilized by the addition of 5.5 g p-FORM powder, whereupon it assayed 19.4 percent DBNPA. A sample of this final preparation was then given a rapid-aging treatment at 50° C., with the following results noted:

| Time, in days after p-FORM addition | % DBNPA Retained |
| --- | --- |
| 4 | 98 |
| 10 | 98 |
| 18 | 97 |
| 25 | 95 |

Second Illustration (Demonstrating addition of EtCA to pre-made mixture of $NH_3$ in TEG-TEG:EtCA ratio of 1.77)

The same apparatus set-up as utilized in the first illustration was again employed. Over a two-hour period at 8°-12° C. a theoretical 17 percent excess (24 g) of $NH_3$ was passed into 200 g of TEG in the reaction flask.

The reactor flask was insulated. In one volume of addition, there was then charged at 8° C. one gram-mole (113 g) of EtCA with constant agitation of the liquid mixture. A 20° temperature rise was noted in one hour. The reaction was permitted to continue with constant stirring, for about 16 hours. After that an additional quantity of gaseous $NH_3$ in an amount calculated to correct for escape to the scrubber to provide a net total of 36 g (100 percent excess) $NH_3$ was put into the system. The residual NH$_3$ and the by-product ethanol were removed by distillation at 200 mm Hg absolute pressure.

Leaving the product CA in solution in the reactor, the intermediate CA was brominated over a one-hour period in the same way and with the same quantities of Br$_2$ and NaBrO$_3$ as in the first illustration. A 20°–37° C. reaction temperature was maintained by an ice bath. After the bromination, 325 g of additional TEG were added to the reaction mass which dissolved a small quantity of solids that had formed.

The resulting DBNPA-containing reaction mass was then neutralized with 10 percent aqueous Na$_2$CO$_3$ to pH 3.5, after which 5.0 g of p-FORM powder (0.5 percent composition loading) were added and mixed thoroughly. The resulting formulation assayed 21.9 percent DBNPA (by iodimetric testing) and weighed 1060 g. Accordingly, the DBNPA yield from the EtCA was 96.4 percent.

Under rapid, 50° C. aging of the formulation, the following stability observations were obtained:

| Time, in days after p-FORM addition | % DBNPA retained | pH |
| --- | --- | --- |
| 0 | 100 | 3.5 |
| 6 | 99 | 3.5 |
| 10 | — | — |
| 17 | 98 | 3.2 |
| 24 | 97 | 3.0 |
| 34 | 90 | 2.5 |

Third Illustration (With a 3.75 ratio of TEG:EtCA)

The procedure of the second illustration was essentially repeated, excepting to dissolve only 19 g (90 percent excess) of the NH$_3$ in 187 g TEG at 18°–21° C. The reactor was insulated and 69.5 g EtCA were added with constant agitation and temperature of 20° C. A temperature rise of 17° C. was noted in ¼ hour then slowly decreased. Analysis of the reaction mass by gas chromatography (i.e., "G.C.") showed that the desired reaction had been essentially completed in ½ hour. After standing overnight (ca. 16 hours), the excess NH$_3$ and the by-product ethanol were removed at reduced pressure (150 mm Hg).

Bromination of the CA to DBNPA, done as in the second illustration, was completed in one hour at 20°–38° C. The DBNPA-containing reaction mass was allowed to stand overnight, after which an additional 150 g of TEG and 50 g of tap water were added to provide the desired DBNPA concentration in the resulting formulation. This adjusted material was then neutralized with 10 percent aqueous Na$_2$CO$_3$ to pH 3.5 and stabilized with 3.0 g p-FORM. The assay, via iodimetry, was 20.55 percent DBNPA on 668 g of product solution formulation, signifying a 92.5 percent yield from the starting EtCA.

The 50° C. rapid-age results were as follows:

| Time, in days after p-FORM addition | % DBNPA retained | pH |
| --- | --- | --- |
| 4 | 99 | 3.5 |
| 18 | 97 | 3.0 |
| 28 | 96 | 3.0 |

Fourth Illustration (Making DBNPA from MeCA)

The procedure of the first illustration was basically repeated.

A mole quantity, 100 g, of MeCA in 200 g TEG was reacted with a 60 percent excess of gaseous NH$_3$ which was added at 23°–28° C. over a period of one hour. Unreacted NH$_3$ and by-product methanol were removed by heating the pot up to 145° C., providing a 40 ml collection of distillate.

Bromination was then performed as in the first illustration using the same proportions of Br$_2$ and aqueous NaBrO$_3$ in the same intermittently alternating manner of charging. This was done, at 28°–38° C., in 1¼ hours. The pH of the resulting liquor at the end of the 1¼-hour period was 3.5, necessitating for proper adjustment thereof an addition of 3 ml of 48 percent aqueous HBr. The reaction mass was stirred for an additional ½ hour to ensure thorough effect from the hydrobromic acid.

Upon completion of the HBr addition, 450 g of TEG was added, whereupon the pH was adjusted to 3.2 with 7.2 g of Na$_2$CO$_3$ in 10 percent aqueous solution after which 5.5 g of p-FORM powder were added to stabilize the formulation.

A 92 percent yield from MeCA was indicated by an iodimetric DBNPA assay of 19.3 percent of the 1165 g of product formulation. Rapid aging at 50° C. gave 94 percent DBNPA retention after 14 days.

Fifth Illustration (Bromination of CA to DBNPA in polyethylene glycol)

Into a suitable reactor there were charged 692 parts of "Polyglycol E-200" polyethylene glycol and 84 parts (1 mole) CA. This was converted to DBNPA by the alternate additions of increments of slightly more than 79 parts (1 mole quantity) of Br$_2$ and 50 parts (almost ⅓ mole) of NaBrO$_3$ in 224 parts of tap water.

The reaction was conducted at 21°–33° C. over a 40-minute period. Toward its finish, it appeared to slow noticeably. To ameliorate this, about 15 parts of concentrated aqueous HBr were added and allowed to continue in the reaction, with constant continued stirring, for another two hours.

The resulting product Rxn Mass was then neutralized with 5.5 parts of 10 percent aqueous Na$_2$CO$_3$ to provide 1245 parts of the final DBNPA formulations. This was divided into three separate portions. The first was stabilized with p-FORM at 0.5 percent concentration. The second portion was treated with ethylenediaminetetracetic acid (i.e., "EDTA") at 0.5 percent concentration. The remaining portion was left in unstabilized condition.

The stabilities of the respective stabilized and unstabilized portions were then given the 50° C. rapid-aging test with the following results obtained:

| Time, in days after preparation | % DBNPA Retained | | |
| --- | --- | --- | --- |
| | Unstabilized | + 0.5% p-FORM | + 0.5% EDTA |
| 10 | 95 | 97 | 97 |
| 18 | 90 | 96.5 | 97 |
| 28 | 84 | 96 | 95 |
| 34 | 79 | 94 | 94 |

The results impressively indicate that the stability of the compositions prepared in accordance with the practice of the present invention are at least about as good as those obtained with other known antimicrobial compositions made by bromination of the CA in water.

This fifth illustration well demonstrates the good stability of a DBNPA formulation resulting from bromination of CA in essentially pure polyethylene glycol with little water present (as a result from that introduced by the Na$_2$BrO$_3$ and HBr reagent additions). Such low water levels appear to tend to materially eliminate inclusion of water-insoluble CA into the DBNPA crystals that are forming in the course of the bromination, causing difficulties in achieving desired reaction completion of the CA. In such instances of potential CA blockage, the stoichiometric quantities of brominating agents that are present could react to form undesired and less stable compounds resulting from the potential N-bromination and/or the addition of bromine across the triple bond of the -CN unit.

Sixth Illustration (Preparation of DBNPA from EtCA in "Polyglycol E-200")

A relatively large resin kettle was employed as the reactor for the entirely in situ procedure. This was outfitted with a pH probe capable of extension in the reaction mass to monitor the Br$_2$-BrO$_3^-$ additions at a pH of 2.0 or below to facilitate rapid reaction and avoid excess BrO$_3^-$ addition.

To the kettle there was initially added 1,000 parts of polyethylene glycol ("E-200") and 320 parts (a 2.83 mole quantity) of EtCA, following which 100 parts (a 5.83 mole quantity) of NH$_3$ were introduced below the liquid surface. After the CA-forming reaction, the excess NH$_3$ and by-product ethanol were removed by steam heating the jacket of the kettle which was simultaneously put under reduced pressure.

Bromination was begun when the reaction mass was free of alcohol as evidenced by gas chromatography. This was done by monitoring the alternate additions of Br$_2$ (440 parts-2.75 moles) and NaBrO$_3$ (138 parts-0.917 mole) in 416 parts of tap water, all accomplished at a pH less than 2. Extra hydrochloric acid (HCl) and HBr were added to facilitate finishing of the bromination via the bromate addition. Then a slight excess of CA was added to decolorize the reaction liquor.

The pH of the resultant product was adjusted to 3.5 with a dilute aqueous Na$_2$CO$_3$ solution, and additional "E-200" was supplied to give a final formulation of 3322 parts. To this was added 16 parts of p-FORM for stabilization, with the final assay showing 19.1 percent DBNPA in the composition. This indicated obtention of a 92 percent overall yield.

Rapid-aging testing at 50° C. of the final antimicrobial composition showed the following stabilities: 97.5 percent retained DBNPA with pH 3.2 after 7 days and 97 percent retained DBNPA after 15 days.

Seventh Illustration (Another preparation of DBNPA from EtCA in "E-200")

Three hundred grams of polyethylene glycol "E-200" in a liter reactor system were purged with an N$_2$ stream. The system was closed and 40 g of liquid NH$_3$ were added dropwise into the stirring glycol in 40 minutes at 15°-28° C.

A mole quantity of EtCA, 113 g, was added over a ½-hour period at 16°-40° C. Immediately thereafter the pressure was cautiously reduced to 200 mm Hg, gradually reducing to 20 mm Hg as the temperature of the liquor was increased over a 3-hour period to 80° C. The theoretical amount of ethanol was recovered.

The reactor was again purged with N$_2$ gas. A catalytic amount of 48 percent aqueous HBr acid was then added. The prepared CA was then brominated to DBNPA via alternate additions of bromine and NaBrO$_3$ solution in stoichiometric amounts.

Bromination was completed in less than 2 hours to a pH of 1.5.

The pH was carefully adjusted to 3.5 by the addition of 10 percent Na$_2$CO$_3$ solution and adjusted to 20.1 percent DBNPA concentration by dilution with polyethylene glycol "E-200". Six grams of p-FORM were added as a stabilizer. The final 1163 g of DBNPA formulation assayed 20.1 percent DBNPA (by iodimetry) for an overall 97 percent yield of DBNPA from the EtCA. Under rapid aging at 50° C., the retention of DBNPA in percent upon successive weekly testing was: 99 (at the end of the first week); 97 (after two weeks); 96 (after three weeks); and 94 (at the end of the fourth week).

Analogous good results are achieved when any or all of the foregoing illustrations are repeated excepting to start with other sub-CA's (including various Alk-CA's) of the Formula (I) and to adjust the process for accommodation of same and the diverse alcohol by-products gotten therefrom; or to employ equivalent reagents as specified in the foregoing for the bromination reaction; or to substitute the glycol solvent with other suitable glycol ingredients; or to employ different temperature and/or pressure conditions to conduct the reaction(s); and/or to conduct one or more of the involved steps in a continuous process.

As indicated in the foregoing, significant elimination of labor and associated minimization of equipment and power requirements are achievable by practice of the present invention, particularly in association with steps one and two when they are integrated and sequentially combined. This is primarily for the reason that solid cakes or other forms of CA are extremely difficult to handle and crush into pulverized material suitable for use. Most often, the labor savings thus realized are on the order of 30-35 percent. Further, the process avoids a serious industrial hygiene problem which arises because of considerable dust creation when CA is crushed for use in the ordinary manner.

Many changes and modifications can readily be made in and adapted to embodiments and practices in accordance with the present invention without departing substantially from its apparent and intended spirit and scope, all in pursuance and accordance with the same as it is set forth and delineated in the hereto-appended claims.

APPENDIX
Listing of References
(With capsulated descriptions of the major pertinent subject matter disclosure of each)

| Ref. No. | Identification and Content |
|---|---|
| | Part I - Preparation of CA or similar reactions |
| (1) | Beilstein's Handbuch, Mainwork, Vol. 2, p. 589 |
| | Suppl. I, Vol. 2, p. 256 |
| | Suppl. II, Vol. 2, pp. 534–5 |
| | Suppl. III, Vol. 2, pp. 1632–3 |
| | Suppl. IV, Vol. 2, pp. 1891–2 |
| | (General summary of preparations and reactions of CA) |
| (2) | Org. Syntheses, 9, 36–7 (1929) (C.A. 23:2151$^9$) |
| | (CA from EtCA via concentrated NH$_4$OH) |
| (3) | Organika, 46–52 (1977) (C.A. 89:146396t) |
| | (CA from MeCA via aminolysis with aqueous NH$_3$) |

APPENDIX
Listing of References
(With capsulated descriptions of the major pertinent subject matter disclosure of each)

| Ref. No. | Identification and Content |
|---|---|
| (4) | Zh. Prikl. Khim., 39(4), 916–919 (1966) (C.A. 65:2216f) (CA from EtCA with NH₄OH) |
| (5) | U.S. Pat. No. 3,668,231 (Rosin) (Discloses CA from methanol solution of butyl cyanoacetate - BuCA - treated with NH₃) |
| (6) | U.S. Pat. No. 3,932,476 (Bergeron) (Amides of fatty acids from ester with NH₃ in anhydrous system) |

Part 2 - Preparation, compositions and/or use of DBNPA

| Ref. No. | Identification and Content |
|---|---|
| (7) | Beilstein's Hanbuch, Mainwork, Vol. 2, pp. 595-6 Suppl. II, Vol. 2, p. 539 Suppl. III, Vol. 2, p. 1641 (General summary of DBNPA preparation) |
| (8) | German Patent No. 2,207,236 (C.A. 77:156334n) (Microbiocide of DBNPA and a halide salt) |
| (9) | Israeli Patent No. 46,112 (C.A. 89:179553v) (DBNPA from treatment of CA with aqueous HBr/NaClO₃) |
| (10) | Japanese Kokai No. 75-24,438 (C.A. 83:109779d) (Mixtures of DBNPA with 1,4-bis(bromoacetoxy)-2-butene as bactericides and fungicides) |
| (11) | Japanese Kokai No. 75-11793 (C.A. 84:100855k) (Algicidal, etc., mixtures of DBNPA with other materials) |
| (12) | U.S. Pat. No. 2,419,734 (Burk) (Plant disease control with DBNPA) |
| (13) | U.S. Pat. No. 3,403,174 (Chance) (DBNPA and formaldehyde react to form the methylol derivative of DBNPA) |
| (14) | U.S. Pat. No. 3,488,734 (Burk) (Br₂ added to 2-CA suspended in certain organic solvents at 20–120° C. forms, inter alia, 2-bromo-2-cyanoacetamide) |
| (15) | U.S. Pat. No. 3,493,658 (Schmidt) (Antimicrobial amounts of DBNPA for treating aqueous preparations) |
| (16) | U.S. Pat. No. 3,557,184 (Toepfl) (DBNPA synthesis and dichlorocyanoacetamides) |
| (17) | U.S. Pat. No. 3,674,610 (Wolf) (Addition of DBNPA and subsequent water-soluble base incorporation in antimicrobial method) |
| (18) | U.S. Pat. No. 3,649,166 (Wolf) (Drycleaning compositions and fabrics cleansed therein sterilized by DBNPA addition) |
| (19) | U.S. Pat. No. 3,689,660 (Burk) (Antimicrobial compositions of DBNPA in triethylene glycol or a polyethylene glycol which may contain water) |
| (20) | U.S. Pat. No. 3,733,332 (Toepfl) Halocyanoacetic acid piperidines and DBNPA synthesis) |
| (21) | U.S. Pat. No. 3,751,444 (Solem) (DBNPA from CA with Br₂ in aqueous solution at 40° C. maximum in presence of soluble bromate and HBr) |
| (22) | U.S. Pat. No. 3,839,583 (Shema) (*Aerobacter Aerogenes* controlled in aqueous systems by synergistic mixture of DBNPA and B-bromo-B-nitrostyrene as #2 agent) |
| (23) | U.S. Pat. No. 3,864,253 (Shema) (Same as Ref. (22) but sodium linear dodecyl benzene sulfonate is #2 agent) |
| (24) | U.S. Pat. No. 3,865,724 (Shema) (Same as Ref. (22) but bis-1,4-bromoacetoxy-2-butene is #2 agent) |
| (25) | U.S. Pat. No. 3,873,444 (Shema) (Same as Ref. (22) but t-butylhydroperoxide is #2 agent) |
| (26) | U.S. Pat. No. 3,896,231 (Shema) (Same as Ref. (22) but hexachlorodimethyl sulfone is #2 agent) |
| (27) | U.S. Pat. No. 3,897,554 (Shema) (Same as Ref. (22) but N-2-nitrobutyl morpholine is #2 agent) |
| (28) | U.S. Pat. No. 3,897,562 (Shema) (Same as Ref. (22) but pentachlorophenol is #2 agent) |
| (29) | U.S. Pat. No. 3,915,685 (Konya) (Microbiocides of DBNPA in an inert carrier with certain haloacetic esters which can also contain polyethylene glycol) |
| (30) | U.S. Pat. No. 3,928,198 (Brink) (* in aqueous systems controlled by composition of DBNPA and 3,3,4,4-tetrachlorotetrahydrothiophene-1,1-dioxide) |
| (31) | U.S. Pat. No. 3,928,575 (Moyle) (Microbiocide of mixed DBNPA and a water-soluble halide) |
| (32) | U.S. Pat. No. 3,929,562 (Shema) (Same as Ref. (22) but mixture of 5-chloro-2-methyl-4-isothiazolin-3-one calcium chloride and 2-methyl-4-isothiazolin-3-one calcium chloride is #2 agent) |
| (33) | U.S. Pat. No. 3,930,015 (Swered) (Same as Ref. (22) but 1,3-dichloroacetone oxime acetate is #2 agent) |
| (34) | U.S. Pat. No. 4,022,605 (Konya) - see also U.S. Re. No. 29,826 (Stabilized DBNPA-containing microbial composition and method using a stabilizing diol and a solvent which may be a polyol and which may also contain a haloacetic ester) |

*Aerobacter aerogenes*

What is claimed is:

1. A method of making cyanoacetamide comprising: reacting with at least about an equimolar proportion of ammonia at a temperature in the range between about 10° C. and about 80° C. an α-cyanoacetate of the formula:

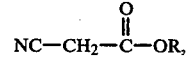

$$NC-CH_2-C-OR, \quad (I)$$

wherein R is selected from the group consisting of an alkyl unit containing from 1 to about 20 carbon atoms and an aryl unit containing from 6 to about 12 carbon atoms, said reaction being conducted with said α-cyanoacetate dissolved in a glycol solvent consisting essentially of a straight-chain polyalkylene glycol or a saturated hydrocarbyl ether thereof that is normally liquid at room temperature and non-reactive with the α-cyanoacetate and ammonia.

2. The method of claim 1 wherein R is an alkyl unit containing not more than about 6 carbon atoms.

3. The method of claim 1 wherein the temperature is in the range of about 20°–50° C.

4. The method of claim 1 conducted under a pressure that is not in excess of about 10 psig.

5. The method of claim 2 wherein R is a methyl or ethyl group.

6. The method of claim 1 wherein the ammonia is employed in a stoichiometric molar excess.

7. The method of claim 2 wherein said glycol solvent is a polyethylene glycol having a weight average molecular weight between about 175 and about 250.

8. A method pursuant to claim 7 wherein said glycol contains water in an amount not in excess of about 25 weight percent, based on the total weight of involved aqueous glycol.

9. A method pursuant to claim 1 including in cooperative addition thereto, the stripping removal of at least substantially all of by-product alcohol formed as a result of said ammoniation reaction from the reaction mass after termination of the reaction.

10. A method in accordance with the method of claim 9 including the subsequent step of brominating the alcohol-freed cyanoacetamide-containing reaction mass, said bromination being effected by the addition of about 1 mole of bromine and about ⅓ mole of an alkali metal bromate per each mole of cyanoacetamide to the reaction mass, while maintaining the reaction mass at a pH that is not greater than about 3.5 and at a temperature of about 0°–50° C. to produce 2,2-dibromo-3-nitrilopropionamide.

11. The method of claim 10 wherein the bromination is conducted at a temperature of between about 10° C. and about 40° C.

12. A method pursuant to claim 10 including the subsequent step of raising the pH of the reaction mass to between about 3 and about 4, stabilizing the 2,2-dibromo-3-nitrilopropionamide by addition thereto of an effective amount up to about 2 weight percent, based on total weight of resulting composition, of a 2,2-dibromo-3-nitrilopropionamide stabilizer, adjusting the glycol solvent content of the reaction mass up to about 60 weight percent, based on total weight of resulting composition, by adding an appropriate amount of the glycol solvent, and adjusting the water content of the reaction mass to between about 20 weight percent and about 99 weight percent, based on total weight of resulting composition, by adding an appropriate amount of water to provide a resulting antimicrobial composition of the recipe:
 0.1–40 weight percent 2,2-dibromo-3-nitrilopropionamide;
 up to 60 weight percent glycol solvent;
 20–99 weight percent water;
 0.5–2 weight percent stabilizer; and
 up to 20 weight percent alkali metal bromide.

13. A method of making 2,2-dibromo-3-nitrilopropionamide comprising:
 dispersing cyanoacetamide in a glycol solvent consisting essentially of a polyethylene glycol having a weight average molecular weight between about 175 and about 250 that is normally liquid at room temperature and non-reactive with the cyanoacetamide, brominating the glycol-dispersed cyanoacetamide-containing reaction mass, said bromination being done by addition of about 1 mole of bromine and about ⅓ mole of an alkali metal bromate per each mole of cyanoacetamide in the reaction mass, while maintaining the reaction mass at a pH value that is not greater than about 3.5 and at a temperature of about 0°–50° C.

14. The method of claim 13 wherein the bromination is conducted at a temperature of between about 10° C. and about 40° C.

15. A method pursuant to claim 13 including the subsequent step of raising the pH of the reaction mass to between about 3 and about 4 by addition of an alkali metal antacid compound, stabilizing the 2,2-dibromo-3-nitrilopropionamide by addition thereto of an effective amount up to about 2 weight percent, based on total weight of resulting composition, of paraformaldehyde, adjusting the glycol solvent content of the reaction mass up to about 60 weight percent, based on total weight of resulting composition, by adding an appropriate amount of the glycol solvent, and adjusting the water content of the reaction mass to between about 20 weight percent and about 99 weight percent, based on total weight of resulting composition, by adding an appropriate amount of water to provide a resulting antimicrobial composition of the recipe:
 0.1–40 weight percent 2,2-dibromo-3-nitrilopropionamide;
 up to 60 weight percent glycol solvent;
 20–99 weight percent water;
 0.5–2 weight percent paraformaldehyde; and
 up to 20 weight percent alkali metal bromide.

* * * * *